United States Patent
Prus et al.

(10) Patent No.: US 10,575,816 B2
(45) Date of Patent: Mar. 3, 2020

(54) CAVITATION LOCALIZATION

(71) Applicants: Oleg Prus, Haifa (IL); Yoav Levy, Hinanit (IL)

(72) Inventors: Oleg Prus, Haifa (IL); Yoav Levy, Hinanit (IL)

(73) Assignee: INSIGHTEC, LTD., Tirat Carmel (IL)

(*) Notice: Subject to any disclaimer, the term of this patent is extended or adjusted under 35 U.S.C. 154(b) by 467 days.

(21) Appl. No.: 15/415,351

(22) Filed: Jan. 25, 2017

(65) Prior Publication Data

US 2018/0206816 A1 Jul. 26, 2018

(51) Int. Cl.
*A61B 8/08* (2006.01)
*A61B 8/00* (2006.01)
*A61B 8/14* (2006.01)

(52) U.S. Cl.
CPC .......... *A61B 8/14* (2013.01); *A61B 8/08* (2013.01); *A61B 8/085* (2013.01); *A61B 8/0808* (2013.01); *A61B 8/4416* (2013.01); *A61B 8/4488* (2013.01); *A61B 8/4494* (2013.01); *A61B 8/481* (2013.01); *A61B 8/5215* (2013.01); *A61B 8/5223* (2013.01); *A61B 8/5292* (2013.01); *A61B 8/54* (2013.01)

(58) Field of Classification Search
CPC .. A61B 8/14; A61B 8/481; A61B 8/08; A61B 8/4494
See application file for complete search history.

(56) References Cited

U.S. PATENT DOCUMENTS

| 5,490,512 A * | 2/1996 | Kwon ............ A61B 8/4494 600/447 |
| 9,226,727 B2 | 1/2016 | Coussios et al. |
| 9,238,152 B2 | 1/2016 | Coussios et al. |

(Continued)

FOREIGN PATENT DOCUMENTS

| WO | 2008062342 | 5/2008 |
| WO | 2008062342 A2 | 5/2008 |

(Continued)

OTHER PUBLICATIONS

Li et al., "A New Active Cavitation Mapping Technique for Pulsed HIFU Applications-Bubble Doppler", IEEE Transactions on Ultrasonics, Ferroelectrics, and Frequency Control vol. 61, issue: 10, (2014 ).

(Continued)

*Primary Examiner* — William J Levicky
(74) *Attorney, Agent, or Firm* — Morgan, Lewis & Bockius LLP

(57) ABSTRACT

Various approaches for detecting microbubble cavitation resulting from ultrasound waves transmitted from an ultrasound transducer include associating at least one time-domain reference signal with microbubble cavitation; causing the transducer to transmit one or more ultrasound pulse; acquiring, in the time domain, an echo signal from microbubbles in response to the transmitted ultrasound pulse(s); correlating at least a portion of the echo signal to at least a corresponding portion of the time-domain reference signal based on similarity therebetween; and detecting the microbubble cavitation based on the corresponding portion of the reference signal.

29 Claims, 13 Drawing Sheets

(56) References Cited

U.S. PATENT DOCUMENTS

| | | | |
|---|---|---|---|
| 2010/0056924 A1* | 3/2010 | Powers | A61B 8/481 600/458 |
| 2010/0318002 A1 | 12/2010 | Prus et al. | |
| 2015/0005756 A1 | 1/2015 | Tillander et al. | |
| 2017/0223207 A1 | 8/2017 | Mihira | |

FOREIGN PATENT DOCUMENTS

| | | |
|---|---|---|
| WO | 2009083557 A1 | 7/2009 |
| WO | 2009138980 | 11/2009 |
| WO | 2010103469 A1 | 9/2010 |
| WO | 2011156624 | 12/2011 |
| WO | 2012042494 | 4/2012 |
| WO | 2014041370 | 3/2014 |
| WO | 2017004562 A1 | 1/2017 |

OTHER PUBLICATIONS

International Search Report, for International Application No. PCT/IB2018/000073, dated Apr. 25, 2018, 14 pages.

\* cited by examiner

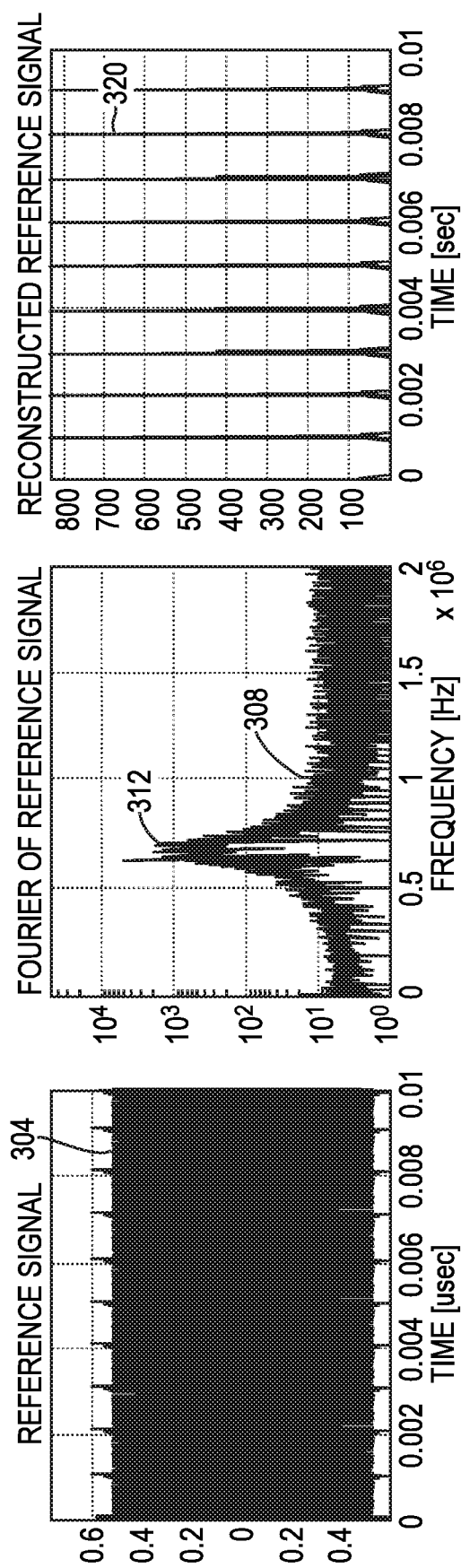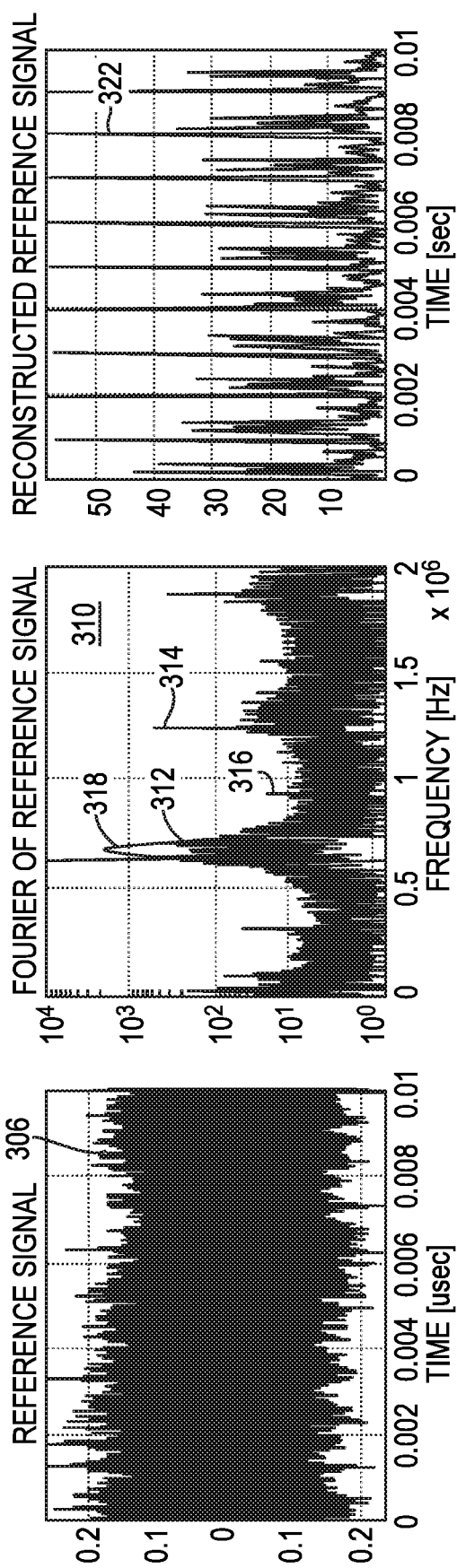

CAVITATION LOCALIZATION

FIELD OF THE INVENTION

The field of the invention relates generally to ultrasound systems and, more particularly, to systems and methods for detecting and locating cavitation caused by microbubbles during an ultrasound procedure.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

During a focused ultrasound procedure or an ultrasound imaging, small gas bubbles (or "microbubbles") may be generated in the liquid fraction of the target tissue, e.g., due to the stress resulting from negative pressure produced by the propagating ultrasonic waves and/or due to rupture of the heated liquid and its accumulation of gas/vapor. Depending upon the amplitude of the applied stress from an acoustic field, the microbubbles may collapse (this mechanism is called "cavitation") and cause various thermal effects in the target and/or its surrounding tissue. For example, at a low acoustic pressure, stable cavitation of microbubbles may be induced to enhance energy absorption at the ultrasound focal region. Stable cavitation can allow tissue within the focal region to be heated faster and more efficiently than would occur in the absence of microbubbles. At a high acoustic pressure, however, unstable (or inertial) cavitation of the microbubbles may be induced, and this may cause undesired bio-effects such as hemorrhage, cell death, and extensive tissue damage beyond that targeted.

Accordingly, there is a need to detect and monitor microbubble cavitation resulting from therapeutic ultrasound waves so as to adjust a treatment plan to achieve desired therapeutic bio-effects on the target tissue without damaging the non-target tissue.

SUMMARY

The present invention provides systems and methods for detection and localization of microbubble cavitation occurring during an ultrasound procedure (such as ultrasound therapy or imaging). In various embodiments, a library of reference signals is acquired using a physical model that simulates acoustic pressure in a simplified tissue model (e.g., water) or in the inhomogeneous tissue that the ultrasound beams, focused on a deeper target region, would traverse. Additionally or alternatively, the library is established based on the reception of echo signals (waves or pulses) from the microbubbles in response to emission of ultrasound signals from an ultrasound transducer array. In one implementation, the ultrasound signal transmitted from the transducer array is a coded pulse (e.g., a chirp signal). The received echo signals that result therefrom are converted to signals at multiple frequencies in the frequency domain, filtered by suitable filters, and then reconstructed in the time domain to improve the resolution and/or signal-to-noise ratios of the reference signals. The reference signals cover various types of expected microbubble cavitation that can be identified using, for example, an ultrasound device, a cavitation detector device and/or an imaging device. In some embodiments, the cavitation location associated with each reference signal is determined based on the elapsed time between the ultrasound signal emission and the reception of the echo signal from the microbubble cavitation. Information about the type and/or location of the cavitation may be stored together with its respective reference signal. It should be noted that the library, in some embodiments, includes portions of reference signals that are associated with the types of microbubble cavitation but not the locations thereof to reduce storage requirements.

During ultrasound treatment or imaging, an echo signal in the time domain received in response to ultrasound signals transmitted from the transducer array to the target region is detected. The received echo signal may be compared and matched against the reference signals in the library to determine the signal similarities therebetween. Once a best-matching reference signal is identified, a microbubble cavitation event is deemed to have occurred and the type and/or location of the cavitation associated with the best-matching reference signal is considered the type and/or location of the cavitation occurring during the ultrasound procedure. Thus, compared with conventional cavitation detection approaches, the current invention allows the detection of cavitation according to the unique nonlinear response of the microbubbles. In addition, the current invention significantly reduces the requirement of signal processing time and complexity by directly comparing the received echo signal and reference signals in the time domain without the need to convert the received echo signals to frequency-domain components and then to filter the frequency components and analyze them in order to determine the presence and/or location of microbubble cavitation.

In various embodiments, the library includes portions of reference signals that are associated with the types of microbubble cavitation but not the locational information thereof (i.e., no or limited information on the elapsed times). During ultrasound treatment or imaging, every portion of the received echo signal in response to the ultrasound transmission is compared and matched against the reference signals in the library. If a portion of the received echo signal matches a reference signal, the type of cavitation associated with the matching reference signal is considered the type of cavitation occurring during the ultrasound procedure. The cavitation location may then be computed based on the elapsed time between the ultrasound emission and the start time of the echo signal portion that matches the reference signal.

Accordingly, in one aspect, the invention pertains to a method of detecting microbubble cavitation resulting from ultrasound waves transmitted from a transducer. In various embodiments, the method includes associating one or more time-domain reference signals with microbubble cavitation; causing the transducer to transmit one or more ultrasound pulse (e.g., a chirped pulse); acquiring, in the time domain, an echo signal from microbubbles in response to the transmitted ultrasound pulse(s); correlating one or more portions of the echo signal to one or more corresponding portions of the time-domain reference signal(s) based on similarity therebetween; and detecting the microbubble cavitation based on the corresponding portion(s) of the reference signal(s). In one implementation, the associating step includes acquiring the reference signal(s) prior to transmission of the ultrasound pulse(s); the acquired reference signal(s) may be in response to a previous ultrasound pulse.

In various embodiments, the method further includes determining a cavitation type and/or a cavitation location based on the corresponding portion of the reference signal. The reference signal is associated, in a database, with information specifying a cavitation type, a cavitation location, and/or an elapsed time between an onset of the ultrasound pulse transmission and a reception time of the portion of the echo signal correlated to the corresponding portion of the reference signal. In addition, the echo signal may be correlated to the corresponding portion of the reference signal using a matched filter. The corresponding portion of the reference signal may be a portion of the echo signal.

In various embodiments, the reference signal is stored as a spectral signature having multiple components at multiple frequencies. The multiple frequencies include sub-harmonic frequencies, harmonic frequencies, and/or ultra-harmonic frequencies of a frequency associated with the ultrasound pulse. In one embodiment, the method further includes applying a signal filter (e.g., a window function) to each component of the spectral signature. The signal filter may be scaled based at least in part on the frequency associated with the component. In addition, after signal filtering, the spectral signature may be converted to a reconstructed signal in the time domain.

The method may further include dividing the transducer into multiple sub-regions, each having multiple transducer elements. In one embodiment, the ultrasound pulse is transmitted by a first sub-region and the echo signal is measured by a second sub-region; the first sub-region is different from the second sub-region. In another embodiment, the ultrasound pulse is transmitted by a first sub-region of the transducer and the echo signal is subsequently acquired by the first sub-region.

In some embodiments, the associating step includes acquiring the reference signal(s) based at least in part on a physical model. The physical model predicts a nonlinear response of the microbubbles to the ultrasound pulse (which may be a coded pulse such as a chirp). In addition, a signal of the nonlinear response is modeled as:

$$\sin\left(K * 2\pi\left(f_1 + \frac{f_2 - f_1}{T}t^*\right)t^*\right),$$

where $f_1$ and $f_2$ represent frequency boundaries of the chirp, T represents a period of the chirp, $t^*$ represents a time variable without a time delay and ranges from 0 to T, and K represents an order (e.g., ½) of the nonlinearity response.

In addition, the method may further include selecting the corresponding portion of the time-domain reference signal; the portion of the echo signal is correlated to the selected corresponding portion of the reference signal based on similarity therebetween. In various embodiments, the correlating step includes shifting the selected corresponding portion of the time-domain reference signal along the echo signal for determining similarity therebetween. In addition, the method further includes determine a cavitation location based on a shift amount of the selected corresponding portion of the time-domain reference signal along the echo signal. Further, the correlating step may include shifting the portions of two or more time-domain reference signals along the echo signal simultaneously or sequentially.

In another aspect, the invention relates to a system of detecting microbubble cavitation. In various embodiments, the system includes an ultrasound transducer; a computer memory including a database relating one or more time-domain reference signals to microbubble cavitation; and a controller configured to: cause the transducer to transmit one or more ultrasound pulses; acquire, in the time domain, an echo signal from microbubbles in response to the transmitted ultrasound pulse(s); correlate one or more portions of the echo signal to one or more corresponding portions of the time-domain reference signal(s) from the database based on similarity therebetween; and detect, using the database, the microbubble cavitation based on the corresponding portion(s) of the reference signal(s). In one implementation, the controller is further configured to acquire the reference signal(s) prior to transmission of the ultrasound pulse(s); the acquired reference signal(s) may be in response to a previous ultrasound pulse.

In various embodiments, the controller is further configured to determine a cavitation type and/or a cavitation location based on the corresponding portion of the reference signal. The reference signal is associated, in the database, with information specifying a cavitation type, a cavitation location, and/or an elapsed time between an onset of the ultrasound pulse transmission and a reception time of the portion of the echo signal correlated to the corresponding portion of the reference signal. In addition, the controller may be further configured to correlate the echo signal to the corresponding portion of the reference signal using a matched filter. The corresponding portion of the reference signal may be a portion of the echo signal. In some embodiments, the system includes a cavitation detection device. The controller is further configured to add entries to the database; each of the entries includes a time-domain signal received by the cavitation detection device and an identified type of microbubble cavitation associated therewith.

In various embodiments, the reference signal is stored as a spectral signature having multiple components at multiple frequencies. The multiple frequencies include sub-harmonic frequencies, harmonic frequencies, and/or ultra-harmonic frequencies of a frequency associated with the ultrasound pulse. In one embodiment, the controller is configured to apply a signal filter (e.g., a window function) to each component of the spectral signature. The controller is further configured to scale the signal filter applied to each component based at least in part on the frequency associated with the component. In addition, the controller is configured to, after applying a signal filter, convert the spectral signature to a reconstructed signal in the time domain.

The controller may be configured to divide the transducer into multiple sub-regions, each sub-region having multiple transducer elements. In one embodiment, the ultrasound pulse is transmitted by a first sub-region and the echo signal is measured by a second sub-region; the first sub-region is different from the second sub-region. In another embodiment, the ultrasound pulse is transmitted by a first sub-region of the transducer and the echo signal is subsequently acquired by the first sub-region.

In some embodiments, the controller is further configured to acquire the reference signal(s) based at least in part on a physical model. The physical model predicts a nonlinear response of the microbubbles to the ultrasound pulse (which may be a coded pulse such as a chirp). In addition, a signal of the nonlinear response is modeled as:

$$\sin\left(K*2\pi\left(f_1 + \frac{f_2-f_1}{T}t^*\right)t^*\right),$$

where $f_1$ and $f_2$ represent frequency boundaries of the chirp, T represents a period of the chirp, $t^*$ represents a time variable without a time delay and ranges from 0 to T, and K represents an order (e.g., ½) of the nonlinearity response.

In addition, the controller may be configured to select the corresponding portion of the time-domain reference signal; the portion of the echo signal is correlated to the selected corresponding portion of the reference signal based on similarity therebetween. In various embodiments, the controller is further configured to shift the selected corresponding portion of the time-domain reference signal along the echo signal for determining similarity therebetween. In addition, the controller is configured to determine a cavitation location based on a shift amount of the selected corresponding portion of the time-domain reference signal along the echo signal. Further, the controller may be configured to shift the portions of two or more time-domain reference signals along the echo signal simultaneously or sequentially.

Another aspect of the invention relates to a method of detecting microbubble cavitation resulting from ultrasound waves transmitted from a transducer. In various embodiments, the method includes associating each of multiple time-domain reference signals with a different type of microbubble cavitation; causing the transducer to transmit one or more ultrasound pulses; acquiring, in the time domain, an echo signal from microbubbles in response to the transmitted ultrasound pulse(s); computing a matching score associated with each reference signal based on similarity between the acquired echo signal and the reference signal and determining whether the matching score is above a threshold; and if so, determining a cavitation type associated with the microbubbles based on the reference signal having the matching score above the threshold; and if not, repeating steps (a)-(d).

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 3B-1 and 3B-2 depict received acoustic signals in response to the generated coded pulses in accordance with various embodiments;

FIGS. 3C-1 and 3C-2 depict received acoustic signals in the frequency domain in accordance with various embodiments;

FIGS. 3D-1 and 3D-2 depict reconstructed reference signals in the time domain in accordance with various embodiments;

DETAILED DESCRIPTION

Figure 1:
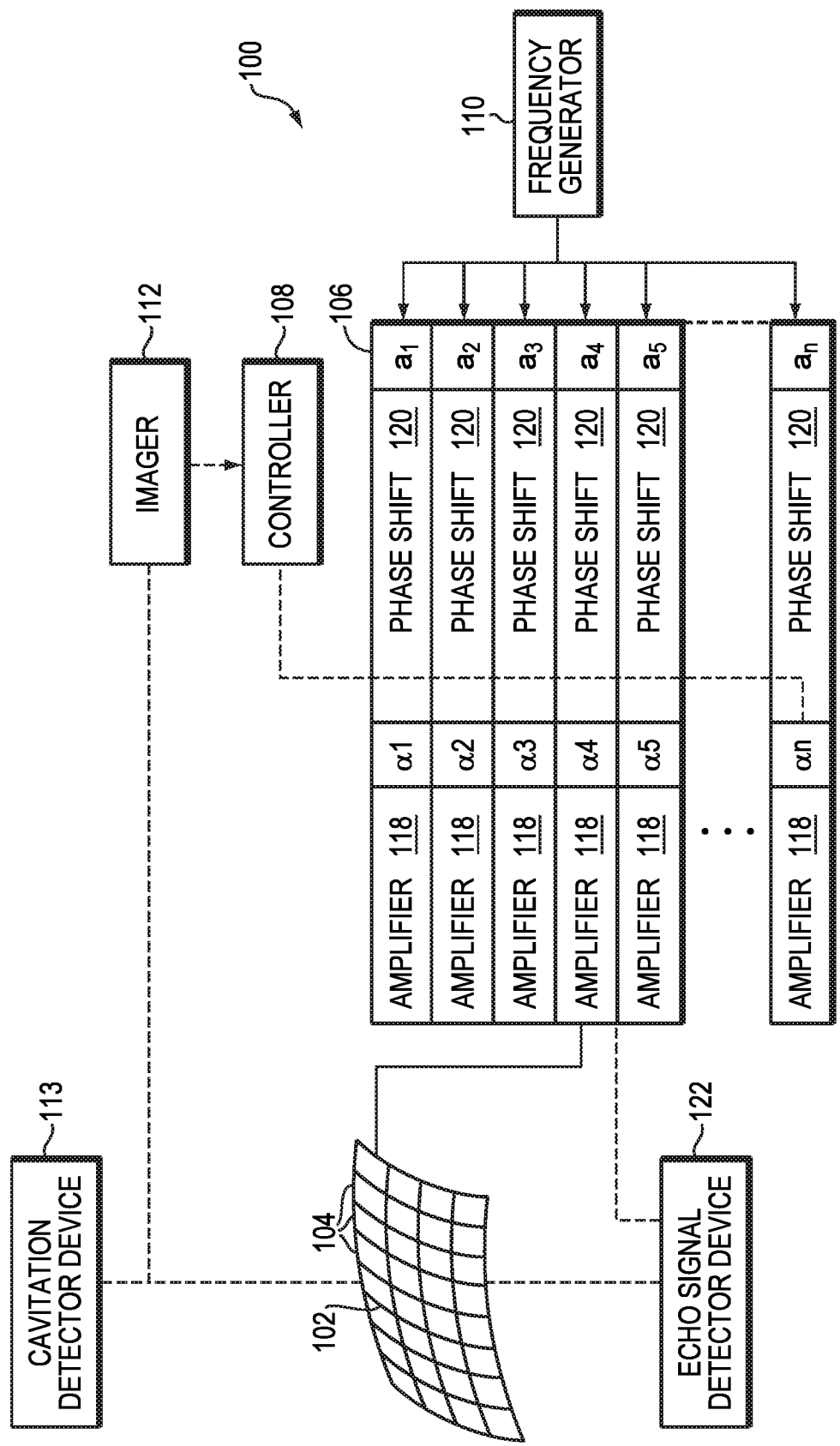
FIG. 1 illustrates a focused ultrasound system in accordance with various embodiments.

FIG. 1 illustrates an exemplary ultrasound system 100 for focusing ultrasound within a patient's brain through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull 114 of a patient 116. The ultrasound system 100 and/or imager 112 may be utilized to detect the presence, type, and/or location associated with microbubble cavitation. Additionally or alternatively, in some embodiments, the system further includes a cavitation detection device (such as a hydrophone or suitable alternative) 113 to detect information associated with microbubble cavitation.

The array 102 may have a curved (e.g., spherical or parabolic) shape suitable for placing it on the surface of the skull 114 or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto a selected region of the patient's brain, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns. In certain embodiments, the computation is based on detailed information about the characteristics (e.g., structure, thickness, density, etc.) of the skull 114 and their effects on propagation of acoustic energy. Such information may be obtained from the imager 112 as further described below. Image acquisition may be three-dimensional or, alternatively, the imager 112 may provide a set of two-dimensional images suitable for reconstructing a three-dimensional image of the skull 114 from which thicknesses and densities can be inferred. Image-manipulation functionality may be implemented in the imager 112, in the controller 108, or in a separate device.

System 100 may be modified in various ways within the scope of the invention. For example, for diagnostic applications, the system may further include a conventional ultrasound detector device (such as a hydrophone) 122 that measures transmitted or reflected ultrasound, and which may provide the signals it receives to the controller 108 for further processing. The reflection and transmission signals may also be used as feedback for the phase and amplitude adjustments of the beamformer 106. The system 100 may contain a positioner for arranging the array 102 of transducer elements 104 with respect to the patient's skull 114. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
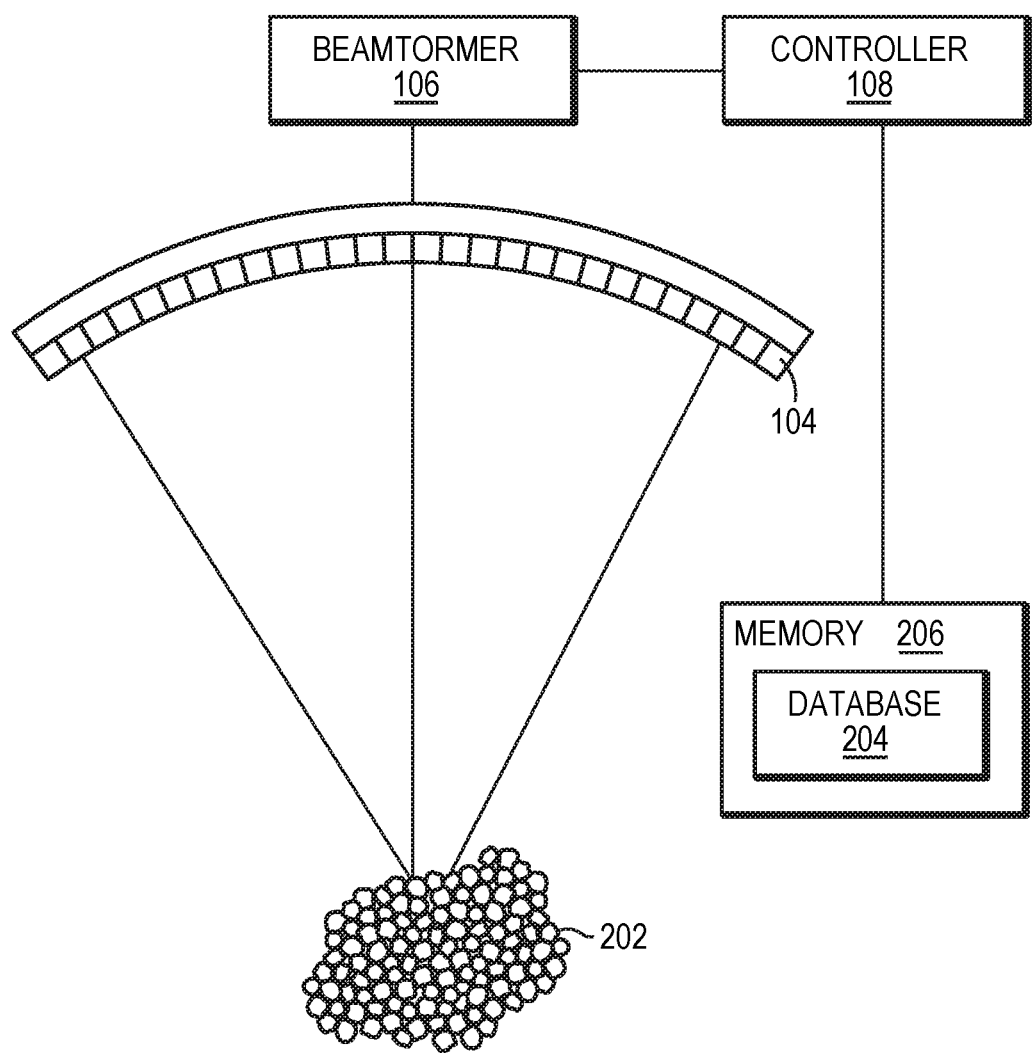
FIG. 2A depicts ultrasound beams delivered to a target tissue region and thereby causing generation of microbubbles in tissue in accordance with various embodiments.

Referring to FIG. 2A, in various embodiments, the acoustic energy emitted by the transducer elements 104 may be above a threshold and thereby cause generation of a bubble or a small cloud of gas bubbles (or "microbubbles") 202 in the liquid contained in the tissue. The microbubbles can be formed due to the negative pressure produced by the propagating ultrasonic waves or pulses or when the heated liquid ruptures and is filled with gas/vapor or when a mild acoustic field is applied on tissue which contains cavitation nucleuses. Generally, at a relatively low acoustic power (e.g., 1-2 Watts above the microbubble-generation threshold), the generated microbubbles undergo oscillation with compression and rarefaction that are equal in magnitude and thus the microbubbles generally remain unruptured. The acoustic response of microbubbles is linear at this low acoustic power and the frequency of ultrasound emitted from the microbubbles is the same as or a harmonic of that of the incident ultrasound waves (i.e., the fundamental frequency or a base harmonic frequency). At a higher acoustic power (e.g., more than 10 Watts above the microbubble-generation threshold), the generated microbubbles undergo rarefaction that is greater than compression, which may cause cavitation and a nonlinear acoustic response of the microbubbles. The acoustic signals returned from cavitation events may include frequencies at the fundamental frequency and/or a harmonic, ultra-harmonic, and/or sub-harmonic of the fundamental frequency. As used herein, the term "fundamental" frequency or "base harmonic" frequency, $f_0$, refers to the frequency (or temporally varying frequency) of the ultrasound waves/pulses emitted from the transducer array 102; the term "harmonic" refers to an integer number of the fundamental frequency (e.g., $2f_0$, $3f_0$, $4f_0$, etc.); the term "ultra-harmonic" refers to a fractional frequency between two nonzero integer harmonics (e.g., $3f_0/2$, $5f_0/4$, etc.); and the term "sub-harmonic" refers to a fractional number between the fundamental frequency and the first harmonic (e.g., $f_0/2$, $f_0/3$, $f_0/4$, etc.).

Figure 2B:
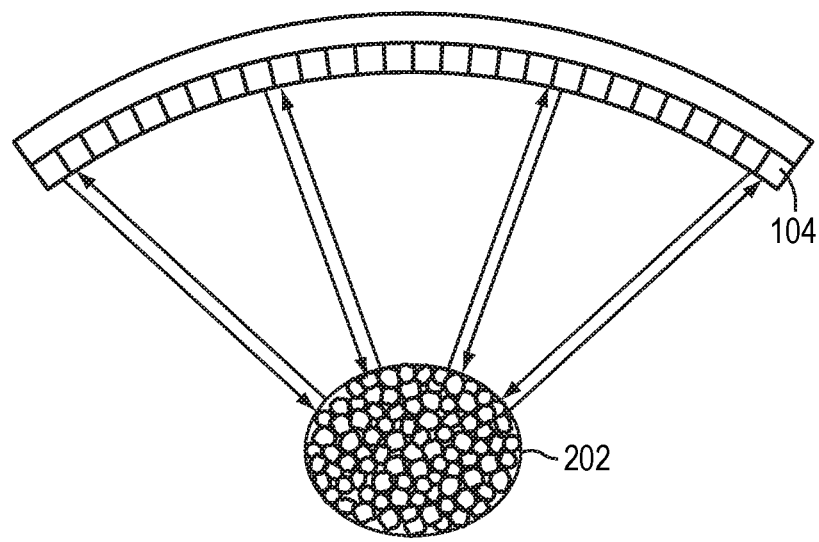
FIGS. 2B-2D depict various configurations of the transducer elements performing a cavitation-detecting method in accordance with various embodiments.
Figure 2C:
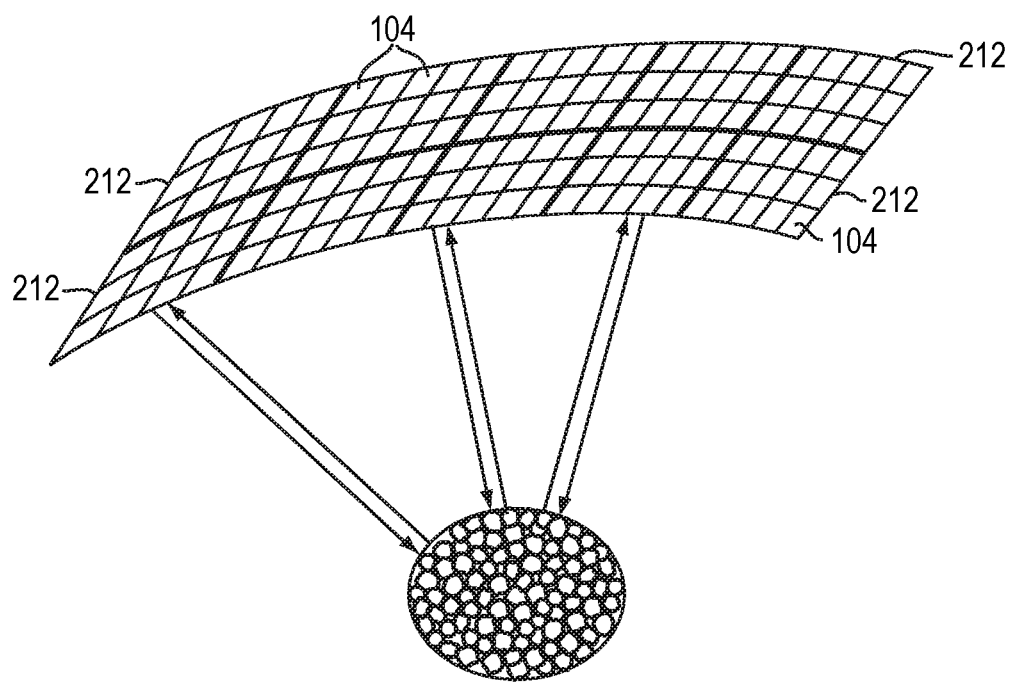
Figure 2D:
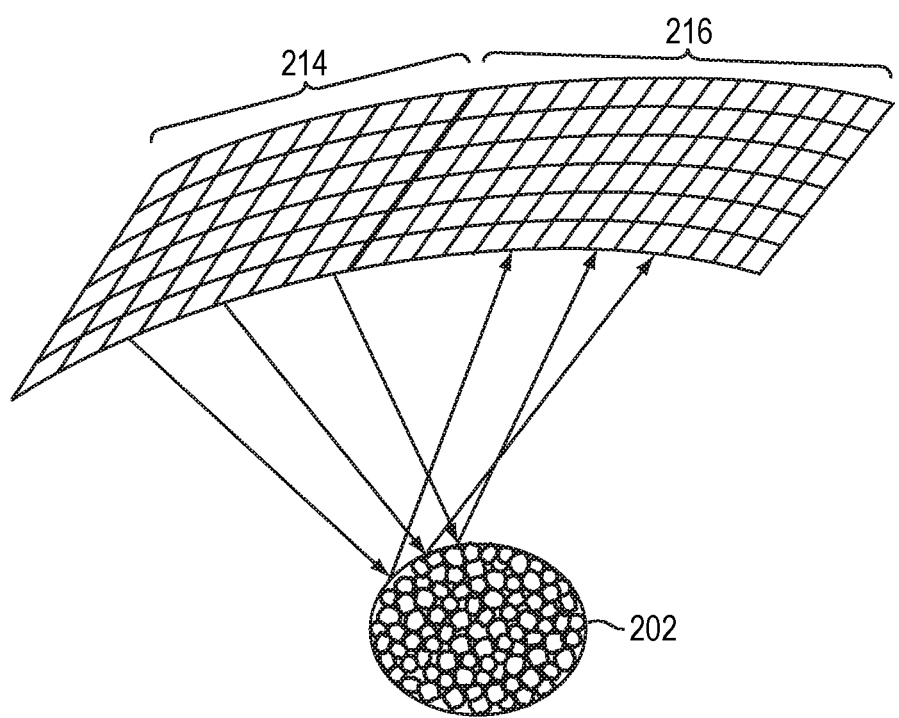

Ultrasound reflections/emission from the microbubbles 202 may be measured using the detector device 122, which then transmits the resulting signals to the controller 108. Alternatively, the transducer elements 104 may possess both transmit and detect capabilities. Referring to FIG. 2B, in one embodiment, each individual transducer element 104 alternates between transmitting ultrasound signals to the microbubbles and receiving ultrasound signals therefrom. For example, all transducer elements 104 may substantially simultaneously transmit ultrasound to the microbubbles 202 and subsequently receive echo signals therefrom. Referring to FIG. 2C, in one implementation, the transducer array is divided into multiple sub-regions 212; each sub-region 212 comprises a one- or two-dimensional array (i.e., a row or a matrix) of transducer elements 104. The sub-regions 212 may be separately controllable, i.e., they are each capable of (i) emitting ultrasound waves/pulses at amplitudes, frequencies and/or phases that are independent of the amplitudes and/or phases of the other sub-regions 212, and (ii) measuring acoustic waves from the microbubbles 202. In one embodiment, the sub-regions 212 are assigned different amplitudes, frequencies and/or phases from one another, and activated, one at a time, to transmit ultrasound to and receive echo signals from the microbubbles 202. Referring to FIG. 2D, in another embodiment, the transducer array is divided into a transmit region 214 and a receive region 216; transducer elements in the transmit region 214 transmit the ultrasound waves/pulses while transducer elements in the receive region 216 receive the echo waves/pulses from the microbubbles 202. The received waves/pulses are then transmitted to the controller 108 for analysis. The transmit region 214 and receive region 216 of the transducer array may be configured in different patterns and shapes at various locations of the transducer array.

Various types of microbubble cavitation may occur during an ultrasound procedure and each type of the cavitation may have its own spectral "signature" that represents the unique nonlinear response of the bubbles. For example, stable cavitation induced at an intermediate acoustic power (e.g., 5 Watts above the microbubble-generation threshold) may produce a strong sub-harmonic response (i.e., having more components at the sub-harmonic frequencies and/or having larger amplitudes of the sub-harmonic frequencies); whereas inertial cavitation induced at a high acoustic power (e.g., 10 Watts above the microbubble-generation threshold) may produce broadband noise. Accordingly, by detecting and analyzing the acoustic signals emitted from the microbubbles, the presence and/or type of cavitation induced in tissue during an ultrasound procedure can be determined.

In various embodiments, the spectral signature associated with each type of cavitation is "learned" based on measurements acquired during previous ultrasound delivery. For example, during a prior ultrasound procedure, the ultrasound system 100, the imager 112 and/or the cavitation detector 113 may detect and monitor the generation of cavitation events in tissue. If a type of cavitation is detected, at least some of the transducer elements 104 and/or a separate detector device 122 are used to measure ultrasound emitted from the microbubbles; the resulting signals may be transmitted to the controller 108 to obtain spectral information associated with the microbubble cavitation. Thus, a mapping between various types of cavitation events and their spectral signatures can be established.

Alternatively, the mapping between various cavitation events and their associated spectral signatures may be established during an earlier treatment sequence of the patient. For example, focused-ultrasound ablation of a tumor may be carried out in two or more phases: a first phase during which the central region of the tumor is targeted, and one or more subsequent phases in which the peripheral regions of the tumor are exposed to ultrasound. Since the risk to healthy tissue surrounding the tumor increases as treatment progresses, so may the need to accurately detect cavitation. Therefore, cavitation detection and spectral analysis as described above may be performed during the first phase to obtain a specific mapping between the types of cavitation and their associated spectral signatures in the patient's tissue. This mapping may be stored in a library and utilized to detect cavitation events during the later phase(s).

Figure 3A:
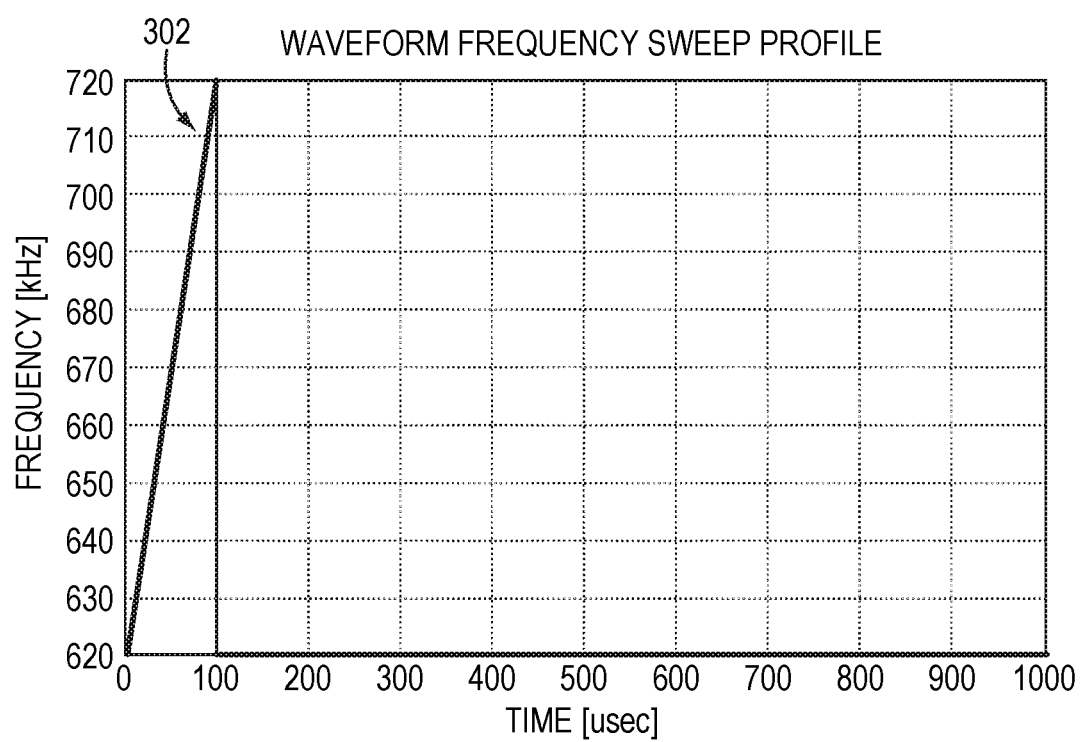
FIG. 3A depicts coded pulses generated by an ultrasound transducer array in accordance with various embodiments.

In one embodiment, during the mapping-establishing process, ultrasound waves/pulses from the transducer elements 104 are emitted at a fixed frequency. Echo signals from the cavitation events in response to the fixed-frequency waves/pulses, however, may sometimes have low resolution and/or signal-to-noise ratios. To improve the quality of the received echo signals, in some embodiments, the radio frequency generator 110 and the beamformer 106 are configured to drive the individual transducer elements 104 to generate coded pulses. For example, the coded pulses may be chirp signals (or sweep signals) in which the frequency increases or decreases with time. Referring to FIG. 3A, in one implementation, the transducer elements generate a 100 µs frequency-modulated (FM) pulse 302 linearly swept from 620 kHz to 720 kHz with a generation period of 1 msec. After emitting the pulse 320, at least some of the transducer elements 104 and/or the separate detector device 122 may detect a calibration signal 304 reflected from the interface between the transducer elements and their surrounding media, and an echo signal 306 reflected/emitted from the microbubble cavitation (as shown in FIGS. 3B-1 and 3B-2). In some embodiments, a Fast Fourier Transform (FFT) approach is used to convert the measured calibration signal 304 and echo signal 306 to spectral signatures 308 and 310, respectively, in the frequency domain (as shown in FIGS. 3C-1 and 3C-2). The calibration signal 304 may have only one frequency peak at the driving frequency 312, whereas the echo signal 306 from the cavitation may have frequency peaks at the driving frequency 312 and its harmonic 314 and ultra-harmonic 316 frequencies.

In various embodiments, optionally, each frequency component in the spectral signatures 308, 310 is filtered by a suitable filter to improve the quality thereof. For example, the filter may be a window function 318. In one implementation, the window function is a Hanning window defined as follows:

$$\text{Hanning window } (f) = \begin{cases} 1 - \cos\left(2\pi \frac{f - f_1}{f_2 - f_1}\right), & f_1 < f < f_2, \\ 0, & \text{otherwise} \end{cases}$$

where f represents the frequency component of the received echo signal and $f_1$ and $f_2$ are the start frequency and end frequency of the coded pulse, respectively. For example, the values of $f_1$ and $f_2$ used to filter the echo signals of the FM pulse 302 are 620 kHz and 720 kHz, respectively.

In some embodiments, the controller 110 computes cross-correlations of the filtered signals 308, 310 with the transmitted signal 302. This may be achieved, for example, by convolving the filtered signals 308, 310 with a conjugated and time-reversed version of the transmitted signal 302. The resulting signals are then reconstructed in the time domain as depicted in FIGS. 3D-1 and 3D-2. For example, the calibration signal 308 and echo signal 310 are reconstructed to form signals 320 and 322, respectively, in the time domain. As shown, the reconstructed echo signal 322 resulting from microbubble cavitation may have a higher signal-to-noise ratio than the original received signal 306. The echo signal 322 may then be stored in a library and used as a reference signal for detecting the presence of microbubble cavitation during an ultrasound procedure.

In various embodiments, the harmonic(s) 314, ultra-harmonic(s) 316 and/or sub-harmonic(s) (not shown) in the spectral signature 310 of the detected echo signal 306 are included when reconstructing the reference signal 322. In one implementation, each harmonic, ultra-harmonic and/or sub-harmonic is processed by its corresponding filter. For example, a filter associated with a $k^{th}$-order harmonic of a fundamental frequency may be defined as follows:

$$\text{filter}^k(f) = A^1\left(\frac{f}{k}\right) \times e^{ik\varphi^1\left(\frac{f}{k}\right)}$$

where $A^1(f)$ and $\varphi^1(f)$ represent an amplitude and a phase of the fundamental frequency filter, and k can be an integer or a fraction. Accordingly, the filter associated with the $k^{th}$-order harmonic is computed by scaling the filter associated with the fundamental frequency based on the order of the harmonic (i.e., k). This scaled harmonic-frequency filter may improve the resolution and/or signal-to-noise ratio of the harmonic, ultra-harmonic and/or sub-harmonic signals, which may be particularly useful for detecting, for example, stable cavitation where the sub-harmonic is strong and/or inertial cavitation where broadband noise increases and more high-order harmonic frequencies occur.

Figure 4:
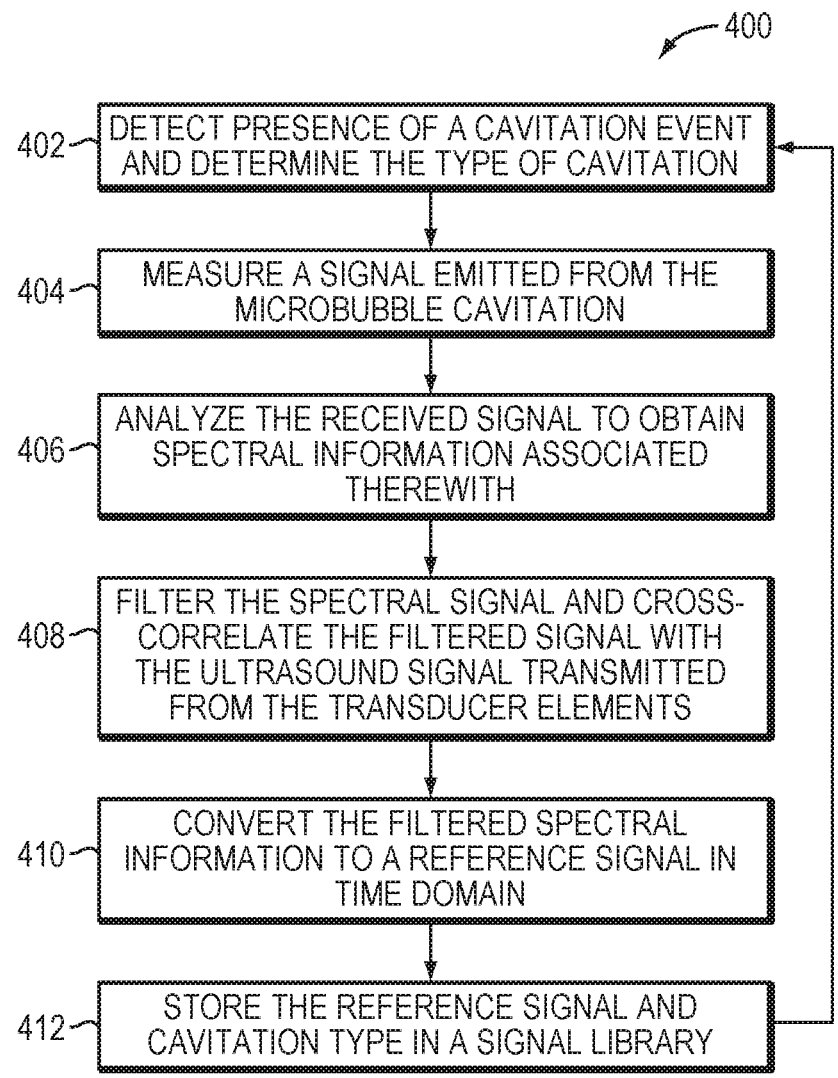
FIG. 4 is a flow chart illustrating an approach for establishing a signal library based on acoustic signal measurements in accordance with various embodiments.

FIG. 4 depicts an approach 400 for establishing a signal library including multiple reference signals each associated with a cavitation type in accordance with various embodiments of the present invention. In a first step 402, an ultrasound system, a cavitation detector and/or an imaging device 112 and/or is utilized to detect the presence of a cavitation event and determine the type of cavitation based on the criteria described above. In a second step 404, if a type of cavitation is detected, at least some of the transducer elements 104 and/or a separate detector device 122 are used to measure a signal emitted from the microbubble cavitation. In a third step 406, the received signal is transmitted to the controller 108 to obtain spectral information associated therewith. In a fourth step 408, the spectral information is filtered and cross-correlated with the ultrasound signal transmitted from the transducer elements 104. In a fifth step 410, a reconstruction approach (such as an inverse Fourier Transform) is utilized to convert the filtered spectral information to a reference signal in the time domain. In a sixth step 412, the reference signal and cavitation type are stored in the signal library. Because different types of cavitation may have different spectral signatures and thus different reference signals, steps 402-412 may be iteratively performed for every type of cavitation until the mapping is complete—i.e., all types of cavitation and their corresponding signals are acquired and stored in the signal library.

It should be noted that each reference signal may include only a portion of the signals emitted by the microbubble cavitation so long as such a portion signal is sufficient to detect cavitation and/or sufficiently different from other reference signals corresponding to other types of cavitation. For example, if a portion of a cavitation signal acquired during a specific stage of a specific cavitation type has a distinct spectral signature different from any signals at any stage of any cavitation type, this portion of cavitation signal alone may be sufficient to detect the presence of the specific cavitation type, and thus other portions of the cavitation signal acquired at other stages may be discarded. How different from other reference signals a signal portion (or signal) must be to serve, effectively, as a proxy for a particular mode of cavitation depends both on the sensitivity of detection and the desired confidence level associated with a positive match. For example, the reference signals may be reliably distinguishable by available detector circuitry, in which case an adequate confidence level is inherent. If fine discrimination among neighboring reference signals (and their associated cavitation modes) is unnecessary for clinical purposes, then the confidence level can be relaxed to reflect tolerance for minor inaccuracies in identification.

Referring again to FIG. 2A, in various embodiments, the signal library is stored in a database 204 in memory 206. The memory 206 may include or consist essentially of one or more volatile or non-volatile storage devices, e.g., random-access memory (RAM) devices such as DRAM, SRAM, etc., read-only memory (ROM) devices, magnetic disks, optical disks, flash memory devices, and/or other solid-state memory devices. All or a portion of the memory 206 may be located remotely from the ultrasound system 100 and/or the imager 112, e.g., as one or more storage devices connected to ultrasound system 100 and/or the imager 112 via a network (e.g., Ethernet, WiFi, a cellular telephone network, the Internet, or any local- or wide-area network or combination of networks capable of supporting data transfer and communication). As utilized herein, the term "storage" broadly connotes any form of digital storage, e.g., optical storage, magnetic storage, semiconductor storage, etc. The database 204 may store the reference signals and the various types of microbubble cavitation (or pointers thereto). For example, the database 204 may be organized as a series of records each of which classifies a reference signal (i.e., a spectral signature) as a particular type of cavitation, and which may contain pointers to the file or files encoding the reference signal in a suitable manner, e.g., as an uncompressed binary file, a .wav file, a compressed signal file, etc. In addition, the record may contain fields for other information (or pointers thereto), including, for example, the location and/or an elapsed time of cavitation associated with each reference signal as further described below.

In various embodiments, a predictive physical model is used to predict the spectral signature associated with microbubble cavitation (e.g., a type and/or location of cavitation) prior to delivery of the ultrasound waves/pulses. The physical model can represent the nonlinear response of the microbubbles for a specific acoustic transmission pattern (e.g., a chirp signal) and/or model the acoustic propagation. For example, the transmission pattern may be a chirp signal defined as follows:

$$\text{transmit}_{signal}(t) = \sin\left(2\pi\left(f_1 + \frac{f_2 - f_1}{T}t\right)t\right),$$

where $f_1$ and $f_2$ are the chirp's frequency range, T is the chirp's period, and t is the time. The nonlinear response of microbubbles to the chirp signal can be modeled as follows:

$$rec_{signal}(t^*, K) = \sin\left(K*2\pi\left(f_1 + \frac{f_2 - f_1}{T}t^*\right)t^*\right),$$

where $t^*$ is a time variable without a time delay and ranges from 0 to T, and K is the nonlinearity response order (e.g., K=½ for a $f_0/2$ sub-harmonic response). In addition, the physical model may predict ultrasound beam paths in tissue based on stored information about the geometry of the transducer elements 104 and their locations and orientations relative to a target region as well as the amplitudes, frequencies and phases of ultrasound waves that will be transmitted from the transducer elements 104. In addition, the physical model may take into account transducer output errors resulting from, for example, transducer elements 104 moving or shifting from their expected location during manufacturing, use and repair and/or as a result of the elements 104 being deformed by heat. Approaches to determining transducer output errors are provided, for example, in U.S. Pat. No. 7,535,794, the contents of which are incorporated herein by reference.

In addition, the physical model may include parameters, such as material properties (e.g., the energy absorption of the tissue, the liquid content of the tissue, or the speed of sound at the employed frequency) along the beam path. The material properties may be collected using the imager 112 as described above and/or other suitable devices. For example, if the tissue surrounding the target and traversed by the ultrasound is a patient's skull, computed tomography (CT) imaging may be used to extract the anatomical characteristics (such as the skull thickness, local bone densities and/or directional or geometrical features including a normal relative to a surface region) of the skull. Methods of creating a local geometric model or mapping of the skull regions 216 are described, for example, in U.S. Patent Publication No. 2010/0179425, the entire disclosure of which is hereby incorporated by reference. In addition, the structural inhomogeneity of the skull may be characterized using an indicator that can be quantified at the microstructure level of the skull; the indicator is determined based on the skull density measured in images acquired using the imager 112. A suitable method is described in U.S. Patent Publication No. 2016/0184026, the entire disclosure of which is hereby incorporated by reference.

Based on the predicted acoustic beam paths and the material properties along the beam path, the physical model may perform acoustic and/or thermal simulations to estimate how different regions reflect and/or absorb different quantities of ultrasound waves/pulses and have different resulting acoustic pressure exerted thereon. Subsequently, the physical model may predict the presence of a cavitation event and its associated spectral signature (such as the frequency components and their weights) based on the predicted acoustic pressure and material properties. The physical model may then combine the various contributions from the frequency components and utilize, for example, an inverse Fourier transform to generate a predicted reference signal for the cavitation event expected to be generated by the acoustic beam path and amplitude being considered. Because different acoustic pressures and/or material properties may result in different types of cavitation, in one embodiment, the physical model generates multiple reference signals, each associated with one type of cavitation. The predicted reference signals and their associated cavitation types are then stored in the signal library in the database 204. Again, each reference signal may include only a portion of the predicted signal that can sufficiently identify the presence and type of the cavitation event.

Figure 5:
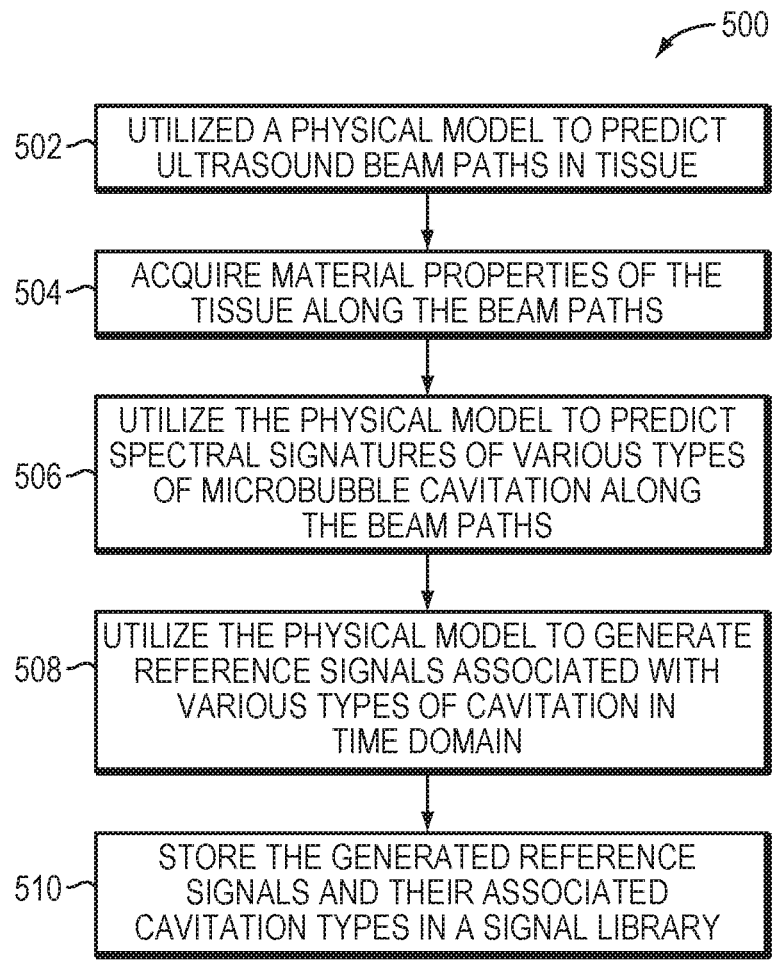
FIG. 5 is a flow chart illustrating an approach for establishing a signal library based on a physical model prediction in accordance with various embodiments.

FIG. 5 depicts an approach 500 for establishing a signal library having multiple reference signals each associated with a cavitation type using a predictive physical model in accordance with various embodiments of the present invention. In a first step 502, the physical model predicts ultrasound beam paths in tissue based on the target location and information about the geometry of the transducer elements 104 and their locations and orientations relative to the target. In a second step 504, the physical model acquires—automatically or by operator input—material properties of the tissue along the beam paths. In a third step 506, the physical model predicts spectral and/or time domain signatures of various types of microbubble cavitation along the beam paths based on the characteristics of the microbubbles and information generated/obtained in steps 502, 504. In a fourth step 508, the physical model generates time-domain reference signals associated with various types of cavitation based on the predicted spectral signatures. In a fifth step 510, the generated reference signals and their associated cavitation types are stored in a signal library in the database 204.

In various embodiments, the reference signals associated with various cavitation types in the time domain are generated based on the spectral signatures predicted by the physical model and spectral signatures measured using the transducer elements and/or a separate detector device. For example, the physical model may first predict the spectral signature and subsequently adjust one or more frequencies and/or their weights in the spectral signature based on the measured echo signals acquired by the transducer elements and/or separate detector device 122. The adjusted spectral signature may then be converted to a reference signal in the time domain for cavitation detection/identification.

Figure 6:
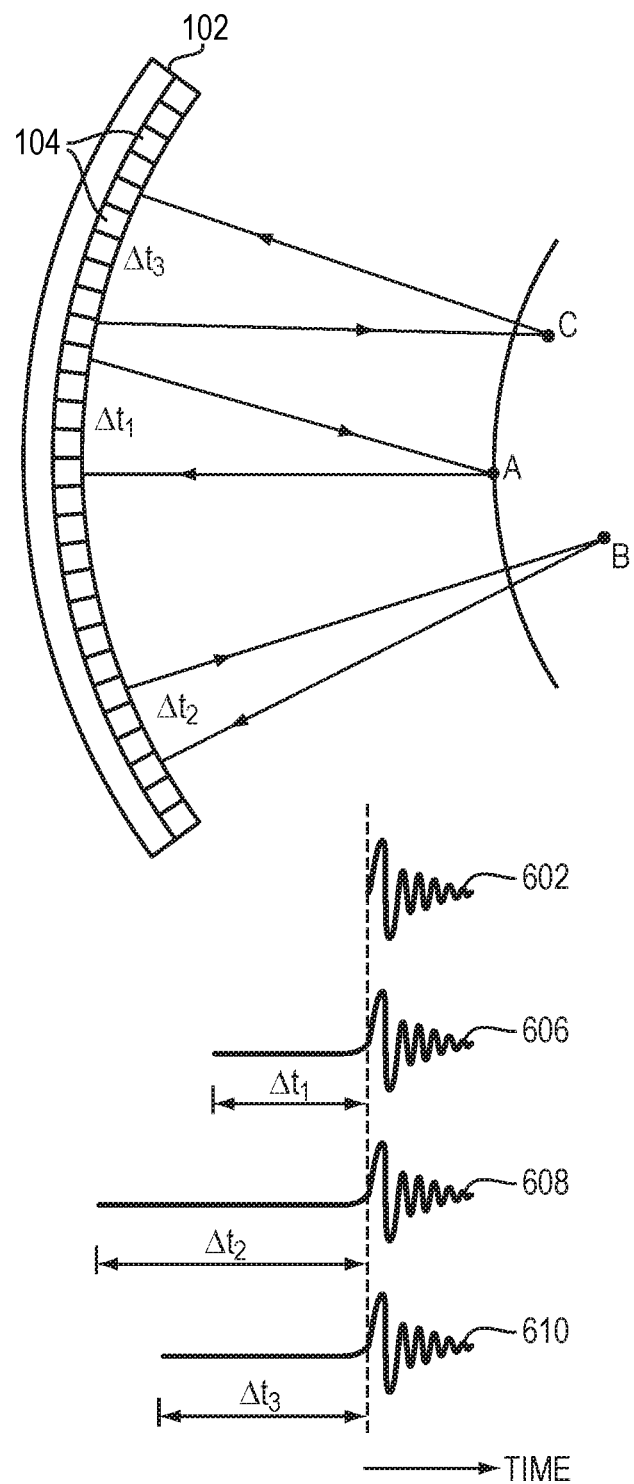
FIG. 6 depicts an approach for generating various reference signals based on the cavitation locations in accordance with various embodiments.

In a preferred embodiment, the reference signals further include the locational information of the cavitation. In one embodiment, an elapsed time, $\Delta t$, between the time of an ultrasound wave/pulse emission and the reception of an echo signal from a cavitation is introduced into the reference signal in the time domain to indicate the location of the cavitation. The elapsed time may be determined based on measurements and/or model predictions as described above; each elapsed time corresponds to a cavitation location. For example, referring to FIG. 6, cavitation occurring at locations A, B and C may be of the same type and thus have the same structure of reference signal 602. But because of their locational difference, cavitation occurring at locations A, B and C may have different elapsed times, $\Delta t_1$, $\Delta t_2$ and $\Delta t_3$, respectively. To include the locational information in the reference signal 602, in various embodiments, the reference signal 602 is "extended" by including the elapsed times, $\Delta t_1$, $\Delta t_2$ and $\Delta t_3$, before its start time 604 in the time domain, thereby creating new reference signals 606, 608, 610 associated with cavitation occurring at locations A, B and C, respectively. Therefore, the reference signals 606, 608, 610 provide information regarding both the cavitation type (by incorporating the reference signal 602) and cavitation locations (by incorporating the elapsed times $t_1$, $\Delta t_2$ and $\Delta t_3$). In various embodiments, each cavitation location is computed based on the elapsed time in the corresponding reference signal and a speed of sound in the tissue. The locational information may then be stored along with its respective reference signal in the signal library in the database 204.

The echo signals emitted from the microbubble cavitation and received by the transducer elements may attenuate when traversing the tissue therebetween. The attenuation rate may be different for difference wave frequencies and/or in different tissue types. As described above, the cavitation response generally includes several frequency components; thus, each frequency component may have an attenuation rate. In addition, a frequency component traversing various types of tissue may also have different attenuation rates. Accordingly, in various embodiments, the predictive physical model adjusts the predicted spectral signatures (and thereby the reference signals) associated with the cavitation by taking into account the attenuation of acoustic waves/ pulses from the cavitation location to the transducer elements, based on the wave/pulse frequencies and/or material properties along the echo paths. Accordingly, multiple reference signals may be generated, each associated with a specific type of cavitation at a specific location (defined, for example, in terms of the distance between the cavitation event and the transducer). Again, these reference signals may be stored in the signal library in the database 204.

It should be stressed that although multiple reference signals may be generated and utilized to detect various locations of microbubble cavitation as described above, one reference signal 602 may be sufficient to achieve the same goal—e.g., using a "moving window" approach as further described below.

The signal library built in the steps described above is used during a subsequent ultrasound procedure for real-time detection and/or location of microbubble cavitation. This means, in some embodiments, that the steps for building the signal library are completed before treatment of the target commences. In other embodiments, the building steps for a particular treatment sequence are taken during an earlier treatment sequence. In various embodiments, during the ultrasound procedure, acoustic signals emitted/reflected from the microbubbles are detected continuously or repeatedly in a discrete manner. The received echo signals are compared against reference signals stored in the signal library using, for example, a matched filter (implemented using cross-correlation) or any other suitable technique. Each reference signal is assigned a matching score; a reference signal is considered matching the received echo signal if its score is above a pre-determined threshold. If more than one reference signal has a matching score above the threshold, the reference signal having the highest matching score is identified as a closest matched reference signal. Once a closest matching reference signal is identified, this signal indicates its associated cavitation type is present and the location of the cavitation can be readily inferred from the previously determined locational information associated with that reference signal.

Figure 7A:
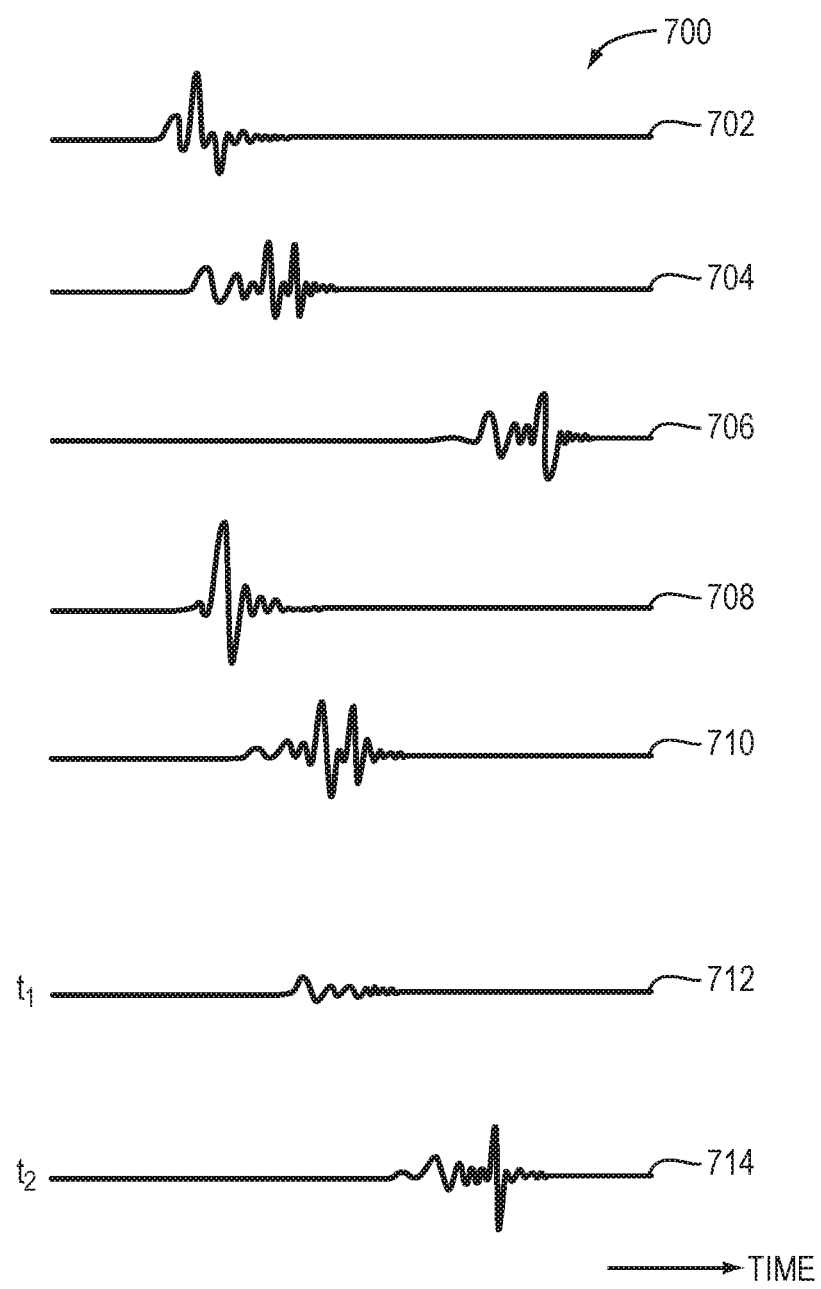
FIG. 7A depicts an approach for comparing a received acoustic signal to reference signals in a signal library in accordance with various embodiments.

For example, referring to FIG. 7A, the signal library 700 may include reference signals 702-710, each corresponding to one type of cavitation at one location. A received acoustic signal 712 from the microbubbles at a time $t_1$ during an ultrasound procedure may be compared against the reference signals 702-710 to determine whether any reference signal matches the received signal 712. If all matching scores assigned to the reference signals 702-710 are below the threshold, it can be assumed that no cavitation of the types associated with the reference signals 702-710 is currently present. This process of searching for matches may continue during the ultrasound procedure. For example, at a time $t_2$, the reference signal 706 may be identified that best matches the received signal 714 (i.e., having a highest matching score above the threshold); thus it can be inferred that the cavitation type and location associated with the reference signal 706 has occurred.

Therefore, unlike conventional approaches that detect presence and/or location of cavitation using signals in the frequency domain, the current invention directly compares the received echo signal from microbubbles and reference signals in the time domain to infer the presence, type and/or location of a cavitation event from the best-matching reference signal; the signal comparison in the time domain is a relatively short process, thereby saving signal processing time. In addition, the current invention advantageously reduces the complexity of required signal processing in conventional approaches where the received echo signals in the time domain have to be converted into frequency components in the frequency domain, followed by comparing each frequency component with the stored record in the database 204 in order to determine the presence and/or location of microbubble cavitation.

Figure 7B:
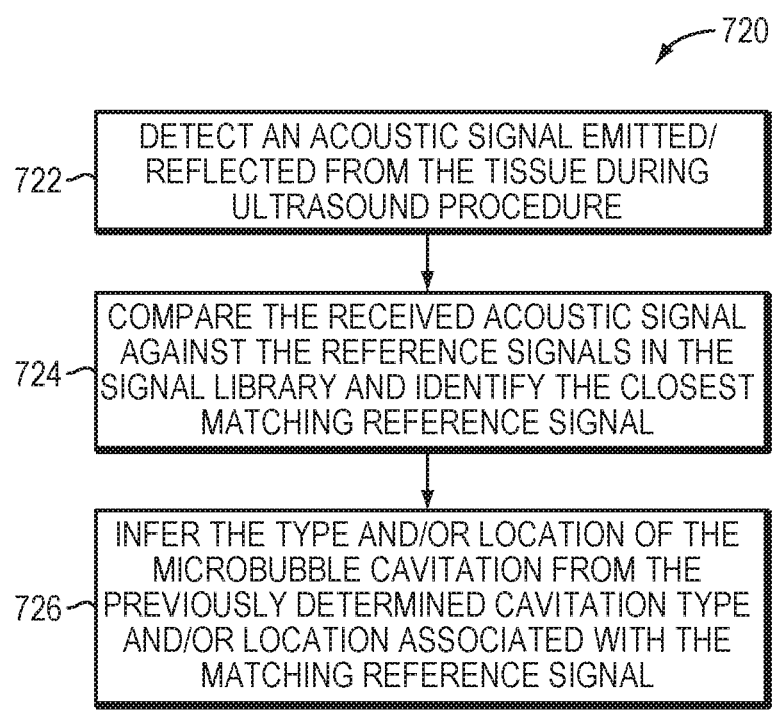
FIG. 7B is a flow chart illustrating an approach for detecting the presence of microbubble cavitation and determining the type and/or location associated therewith in accordance with various embodiments.

FIG. 7B illustrates methods 720 for determining the real-time presence, type and/or location of microbubble cavitation using a signal library built as described above in accordance with various embodiments. In a first step 722, during an ultrasound procedure, an acoustic signal emitted/reflected from the tissue is detected using a portion of the transducer array and/or a separate detection device 122. In a second step 724, the received acoustic signal is compared against the reference signals in the signal library, and the closest match is identified. Once a matching reference signal has been identified, the type, and location of the microbubble cavitation can be readily inferred from the previously determined cavitation type and location associated with that reference signal (step 726).

Figure 8A:
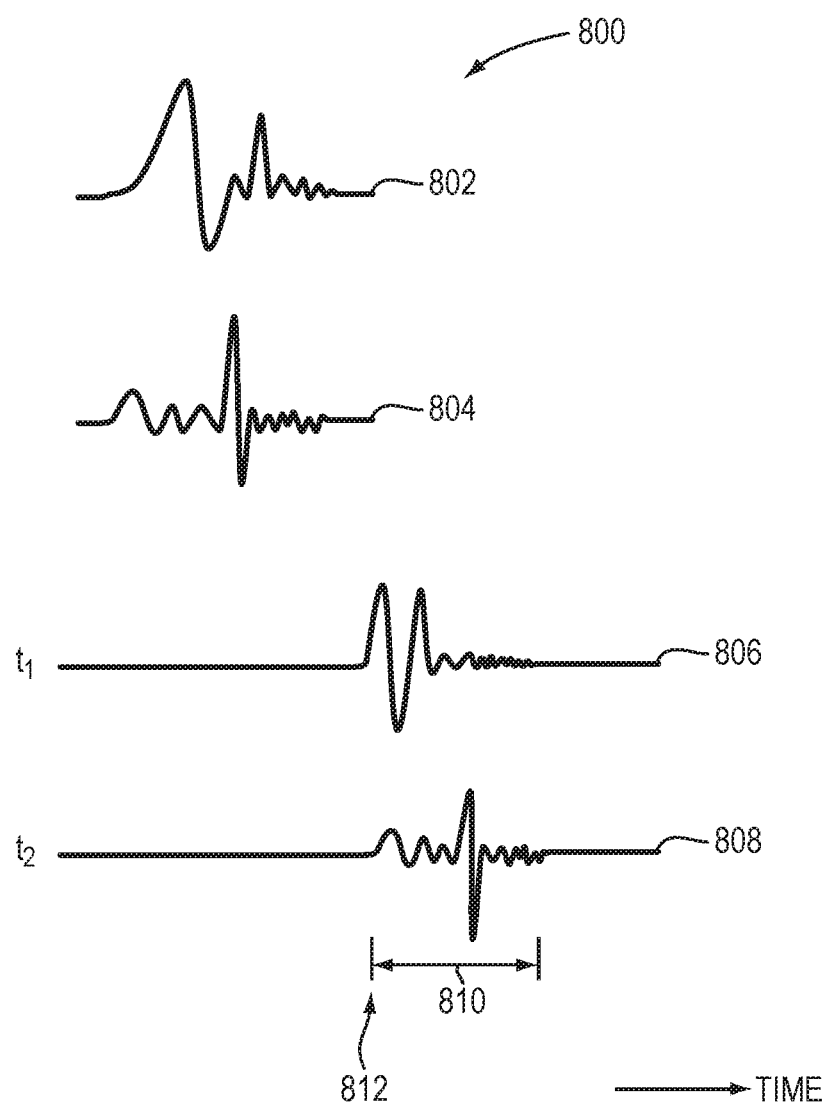
FIG. 8A depicts an approach for comparing a received acoustic signal to reference signals in a signal library in accordance with various embodiments.

In various embodiments, the signal library includes one or more reference signals that are portions of the received acoustic signals; each portion corresponds to one type of cavitation. It should be understood that a "portion" of a signal can refer to a part of a signal or to the entire signal, although for computational efficiency it is desirable to use the minimum amount of a signal necessary to achieve a reliable match to a detected signal so as to reveal the type of cavitation. For example, the signal portion may be the part of a reference signal that most uniquely or reliably characterizes the type of cavitation. Upon receiving an echo signal from the microbubbles, the reference signal acts as a "window" that can be moved along the received signal for determining the presence and type of the cavitation. For example, referring to FIG. 8A, the signal library 800 may include reference signals 802, 804, each corresponding to one type of cavitation. An acoustic echo signal 806 received from the microbubbles at a time $t_1$ during an ultrasound procedure may be compared against the reference signals 802, 804 to determine whether any reference signal matches any portion of the received signal 806. If no reference signal is found to match to any portion of the received signal 806, it can be inferred that no cavitation of the types associated with the reference signals 802, 804 is currently present. If the received acoustic echo signal (for example, a signal 808 received at a time $t_2$) includes a portion 810 that is identified to match the reference signal 802, it indicates that the cavitation type associated with the reference signal 802 has occurred. Additionally, in various embodiments, the cavitation location associated with the received signal 808 is computed based on the speed of sound in the tissue medium and the elapsed time between the onset of ultrasound emission and the start time 812 of the portion 810 that matches the reference signal 804.

Because acoustic attenuation may be different for waves/pulses having different frequencies and/or traversing tissue with different material properties, it may sometimes be challenging to identify all cavitation signatures in the reference signals prior to the ultrasound procedure. Using portions of reference signals as "moving windows" reduces the complexity by eliminating the need to encode locational information into the reference signals. More specifically, the cavitation location may be identified using a time-of-flight approach—i.e., using the time a signal is transmitted by the transducer elements, the time the matching portion 810 is detected by the transducer elements, and the speed of sound through the affected tissue. Because this real-time determination of the cavitation location reflects the effects of varying tissue properties on the echo beam paths, it may provide more accurate locational information than techniques based on, for example, estimates using a generic speed of sound.

Figure 8B:
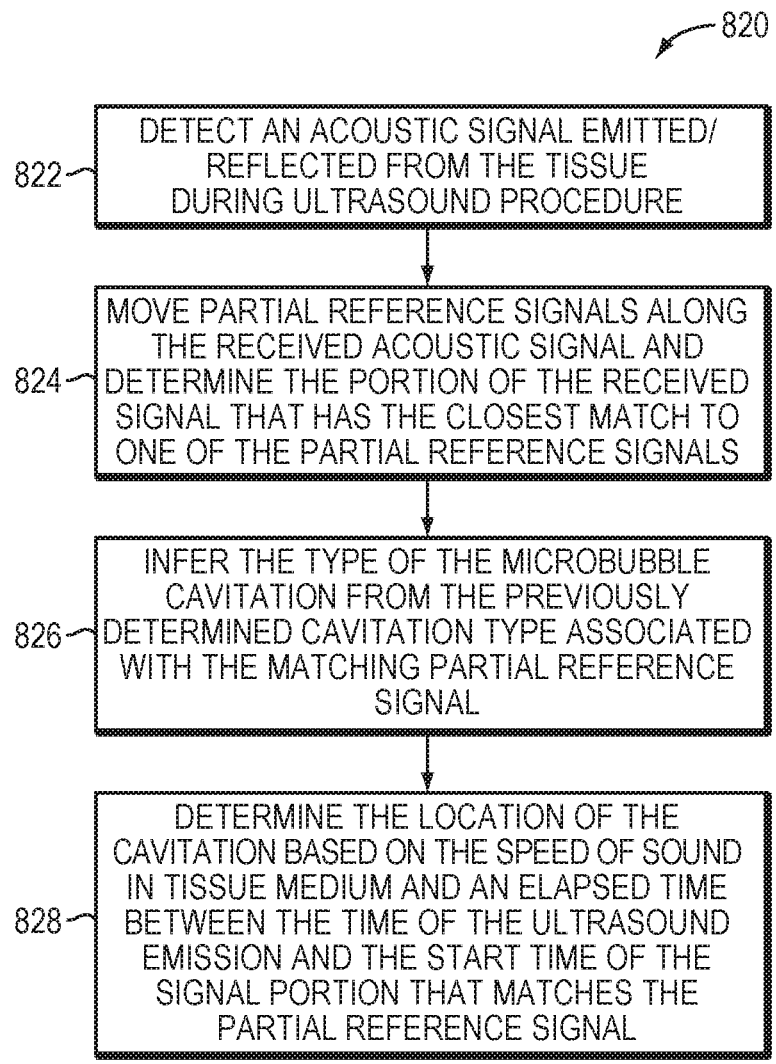
FIG. 8B is a flow chart illustrating an approach for detecting the presence of microbubble cavitation and determining the type and/or location associated therewith in accordance with various embodiments.

FIG. 8B illustrates methods 820 for determining the real-time presence, type and/or location of microbubble cavitation using a signal library having portions of reference signals corresponding to various types of cavitation in accordance with various embodiments. In a first step 822, during an ultrasound procedure, an emitted acoustic signal reflected from the tissue is detected using a portion of the transducer array and/or a separate detection device 122. In a second step 824, one or more portions of reference signals serve as windows moving along the received acoustic signal; the portion of the received signal that has the closest match to one of the portions of reference signals is identified. In other words, each type of cavitation is associated with a portion of signals indicative of that type of cavitation, and a received signal is simultaneously or sequentially analyzed against multiple signal portions in a moving-window fashion to determine which of multiple cavitation types may be present. Once again, each portion may be a single reference signal or more than one reference signal indicative of a particular cavitation type.

Once a portion of the received signal matching a signal within one of the portions of reference signals has been identified, the type of the microbubble cavitation can be assumed to correspond to the cavitation type associated with that reference signal (in a third step 826). In addition, the location of the cavitation can be determined based on the speed of sound in the tissue medium and an elapsed time between the ultrasound emission and the start time of the signal portion that matches the reference signal (in a fourth step 828).

In general, functionality for detecting and/or locating the microbubble cavitation in the tissue, including, analyzing signals received from the microbubbles in response to ultrasound transmitted from the transducer array, acquiring reference signals associated with various cavitation types and/or locations based on acoustic signal measurements and/or a physical model prediction, establishing a signal library, identifying a reference signal in the library matching the received signal during an ultrasound procedure, inferring the cavitation type and/or location from the identified matching reference signal, and/or computing cavitation location based on the speed of sound in tissue medium and an elapsed time, as described above, whether integrated within a controller of the imager, a cavitation detection device 113 and/or an ultrasound system, or provided by a separate external controller or other computational entity or entities, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system of detecting microbubble cavitation, the system comprising:
   an ultrasound transducer;
   a computer memory including a database relating at least one time-domain reference signal to microbubble cavitation, wherein the at least one time-domain reference signal is acquired based on (i) a physical model simulating acoustic pressure in a simplified tissue model or in an inhomogeneous tissue located between the ultrasound transducer and microbubbles or (ii) a response to a first ultrasound pulse transmitted from the ultrasound transducer; and
   a controller configured to:
      cause the transducer to transmit at least a second ultrasound pulse;
      acquire, in the time domain, an echo signal from microbubbles in response to the transmitted second ultrasound pulse;
      correlate, in the time domain, at least a portion of the echo signal to at least a corresponding portion of the time-domain reference signal from the database based on similarity therebetween; and
      detect, using the database, the microbubble cavitation associated with the echo signal based at least in part on the corresponding portion of the reference signal.

2. A method of detecting microbubble cavitation resulting from ultrasound waves transmitted from a transducer, the method comprising:
   acquiring at least one time-domain reference signal based on (i) a physical model simulating acoustic pressure in a simplified tissue model or in an inhomogeneous tissue located between the transducer and microbubbles or (ii) a response to a first ultrasound pulse transmitted from the transducer;
   associating the at least one time-domain reference signal with microbubble cavitation;
   causing the transducer to transmit at least a second ultrasound pulse;
   acquiring, in the time domain, an echo signal from microbubbles in response to the transmitted second ultrasound pulse;
   correlating, in the time domain, at least a portion of the echo signal to at least a corresponding portion of the time-domain reference signal based on similarity therebetween; and
   detecting the microbubble cavitation associated with the echo signal based at least in part on the corresponding portion of the reference signal.

3. The method of claim 2, wherein the reference signal is associated, in a database, with information specifying at least one of (i) a cavitation type or (ii) a cavitation location.

4. The method of claim 3, wherein the cavitation type associated with the reference signal is determined using at least one of an ultrasound detection device, a cavitation detector device or an imaging device.

5. The method of claim 3, further comprising determining at least one of the cavitation type or the cavitation location associated with the echo signal based on the corresponding portion of the reference signal.

6. The method of claim 5, wherein the cavitation location associated with the echo signal is determined based at least in part on an elapsed time between an onset of the at least second ultrasound pulse transmission and a reception time of the portion of the echo signal correlated to the corresponding portion of the reference signal.

7. The method of claim 2, wherein the echo signal is correlated to the corresponding portion of the reference signal using a matched filter.

8. The method of claim 2, wherein the first ultrasound pulse is transmitted from the transducer prior to the at least second ultrasound pulse is transmitted from the transducer.

9. The method of claim 2, wherein the at least one reference signal is stored as a spectral signature having a plurality of components at a plurality of frequencies.

10. The method of claim 9, wherein the plurality of frequencies comprises at least one of sub-harmonic frequencies, harmonic frequencies, or ultra-harmonic frequencies of a frequency associated with the at least second ultrasound pulse.

11. The method of claim 9, further comprising applying a signal filter to each component of the spectral signature.

12. The method of claim 11, wherein the signal filter comprises a window function.

13. The method of claim 11, wherein the signal filter applied to each component is scaled based at least in part on the frequency associated with the component.

14. The method of claim 11, further comprising, after signal filtering, converting the spectral signature to a reconstructed signal in the time domain.

15. The method of claim 2, further comprising dividing the transducer into a plurality of sub-regions, each sub-region comprising a plurality of transducer elements, wherein the first or the at least second ultrasound pulse is transmitted by a first sub-region and the echo signal is measured by a second sub-region, the first sub-region being different from the second sub-region.

16. The method of claim 2, further comprising dividing the transducer into a plurality of sub-regions, each sub-region comprising a plurality of transducer elements, wherein the first or the at least second ultrasound pulse is transmitted by a first sub-region of the transducer and the echo signal is subsequently acquired by the first sub-region.

17. The method of claim 2, wherein the first or the at least second ultrasound pulse is a chirped pulse.

18. The method of claim 2, wherein the first ultrasound pulse is a portion of the at least second ultrasound pulse and the corresponding portion of the reference signal is a portion of the echo signal.

19. The method of claim 2, wherein the physical model predicts a nonlinear response of the microbubbles to the first ultrasound pulse.

20. The method of claim 19, wherein the first ultrasound pulse comprises a coded pulse.

21. The method of claim 20, wherein the coded pulse is a chirp.

22. The method of claim 21, wherein a signal of the nonlinear response is modeled as:

$$\sin\left(K*2\pi\left(f_1 + \frac{f_2-f_1}{T}t^*\right)t^*\right),$$

where $f_1$ and $f_2$ represent frequency boundaries of the chirp, T represents a period of the chirp, t* represents a time variable without a time delay and ranges from 0 to T, and K represents an order of the nonlinearity response.

23. The method of claim 22, wherein $K=\frac{1}{2}$.

24. The method of claim 2, further comprising selecting the corresponding portion of the at least one time-domain reference signal, wherein the at least a portion of the echo signal is correlated to the selected corresponding portion of the reference signal based on similarity therebetween.

25. The method of claim 24, wherein the correlating step comprises shifting the selected corresponding portion of the at least one time-domain reference signal along the echo signal for determining similarity therebetween.

26. The method of claim 25, further comprising determining a cavitation location based on a shift amount of the selected corresponding portion of the at least one time-domain reference signal along the echo signal.

27. The method of claim 24, wherein the correlating step comprises shifting the portions of at least two time-domain reference signals along the echo signal simultaneously.

28. The method of claim 24, wherein the correlating step comprises shifting the portions of at least two time-domain reference signals along the echo signal sequentially.

29. A method of detecting microbubble cavitation resulting from ultrasound waves transmitted from a transducer having a plurality of transducer elements, the method comprising:
(a) acquiring a plurality of time-domain reference signals based on (i) a physical model simulating acoustic pressure in a simplified tissue model or in an inhomogeneous tissue located between the transducer and microbubbles or (ii) a response to a first ultrasound pulse transmitted from the transducer;
(b) associating each of the plurality of time-domain reference signals with a different type of microbubble cavitation;
(c) causing the transducer to transmit at least a second ultrasound pulse;
(d) acquiring, in the time domain, an echo signal from microbubbles in response to the transmitted second ultrasound pulse;
(e) computing, in the time domain, a matching score associated with each reference signal based on similarity between the acquired echo signal and the reference signal and determining whether the matching score is above a threshold; and
if so, determining a cavitation type associated with the microbubbles for the echo signal based at least in part on the reference signal having the matching score above the threshold;
if not, repeating steps (b)-(e).

* * * * *